United States Patent
Dahms et al.

(10) Patent No.: US 8,716,214 B2
(45) Date of Patent: May 6, 2014

(54) COMPOSITIONS FOR THE TARGETTED RELEASE OF FRAGRANCES AND AROMAS

(75) Inventors: Gerd Dahms, Duisburg (DE); Andreas Jung, Duisburg (DE); Holger Seidel, Duisburg (DE)

(73) Assignee: OTC GmbH, Oberhausen (DE)

( * ) Notice: Subject to any disclaimer, the term of this patent is extended or adjusted under 35 U.S.C. 154(b) by 1354 days.

(21) Appl. No.: 10/555,529

(22) PCT Filed: May 7, 2003

(86) PCT No.: PCT/EP03/04788
§ 371 (c)(1),
(2), (4) Date: Nov. 22, 2006

(87) PCT Pub. No.: WO2004/098555
PCT Pub. Date: Nov. 18, 2004

(65) Prior Publication Data
US 2007/0105746 A1    May 10, 2007

(51) Int. Cl.
*A61L 9/04* (2006.01)
*C11D 3/50* (2006.01)

(52) U.S. Cl.
USPC ............. 512/4; 512/1; 424/78.02; 424/78.03; 424/417; 424/450; 424/490; 516/21; 516/22; 264/4; 264/4.1; 264/4.4; 264/4.32; 264/4.33

(58) Field of Classification Search
USPC .................. 424/450, 78.02, 78.03, 417, 490; 514/919; 516/21, 22; 264/4.32, 4.33, 4, 264/4.1, 4.4; 512/4, 1; 239/53, 55
See application file for complete search history.

(56) References Cited

U.S. PATENT DOCUMENTS

| | | | |
|---|---|---|---|
| 4,226,890 A | 10/1980 | Howard | |
| 5,185,155 A | 2/1993 | Behan et al. | |
| 5,288,423 A * | 2/1994 | Behan et al. ................ | 510/119 |
| 5,500,223 A | 3/1996 | Behan et al. | |
| 5,589,448 A * | 12/1996 | Koerner et al. ............. | 510/284 |
| 5,667,800 A * | 9/1997 | De Vringer ................. | 424/450 |
| 5,788,975 A * | 8/1998 | Laversanne et al. ......... | 424/417 |
| 5,985,255 A * | 11/1999 | Vanlerberghe et al. .... | 424/70.28 |
| 6,171,600 B1 | 1/2001 | Dahms | |
| 6,589,562 B1 | 7/2003 | Shefer et al. | |
| 6,653,277 B1 | 11/2003 | Golz-Berner et al. | |
| 2003/0180235 A1 | 9/2003 | Grisoni et al. | |
| 2006/0134222 A1 * | 6/2006 | Jugla ............................ | 424/490 |

FOREIGN PATENT DOCUMENTS

| | | |
|---|---|---|
| CA | 2369594 A1 | 11/2000 |
| DE | 10016155 A1 | 1/2001 |
| DE | 101 52 898 A1 | 4/2003 |
| EP | 0 466 235 A1 | 1/1992 |
| EP | 0 478 326 A1 | 4/1992 |
| EP | 1 243 323 A1 | 9/2002 |
| EP | 1243323 B1 | 9/2002 |
| EP | 1 254 651 A1 | 11/2002 |
| EP | 1337227 B1 | 8/2003 |
| EP | 1337231 B1 | 8/2003 |
| JP | 2002-317192 A | 10/2002 |
| WO | WO-95/15143 A2 | 6/1995 |
| WO | WO-95/19707 A1 | 7/1995 |
| WO | WO-99/43777 A1 | 9/1999 |
| WO | WO-00/67728 A2 | 11/2000 |
| WO | WO-00/72804 A2 | 12/2000 |
| WO | WO-02/15862 A1 | 2/2002 |
| WO | 02/26272 A1 | 4/2002 |
| WO | WO-02/26272 A1 | 4/2002 |
| WO | 02/43671 A2 | 6/2002 |
| WO | 02/43673 A2 | 6/2002 |
| WO | 02/45575 A2 | 6/2002 |
| WO | 02/50230 A1 | 6/2002 |
| WO | WO-02/45575 A2 | 6/2002 |
| WO | WO-02/50230 A1 | 6/2002 |
| WO | WO-02/076603 A1 | 10/2002 |
| WO | 2004082660 A1 | 9/2004 |

OTHER PUBLICATIONS

Benton et al. Lyotropic Liquid-Crystalline Phases and Dispersions in Dilute Anionic Surfactant-Alcohol-Brine Systems. J. Physical Chemistry, vol. 87, pp. 4981-4991 (1983).*
JP06-269656; Sep. 27, 1994; Abstract Only (1 page).
JP06-269656; Sep. 27, 1994; Machine Translation (9 pages).
F. T. Tadros: Applied Surfactants; Wiley-VCH; Weinheim, Germany, 2006; pp. 53, 59-61, 596-598.

* cited by examiner

*Primary Examiner* — Michael L Leonard
(74) *Attorney, Agent, or Firm* — Gudrun E. Huckett

(57) ABSTRACT

In a fragrance and/or aroma composition for the targeted release of fragrances and/or aromas in the form of a solid lipid nanoparticle (SLN) dispersion, in which lipid-based nanoparticles are present which are stabilized by an emulsifier monolayer, one or more membrane layers or other auxiliaries, the fragrances and/or aromas are included in the nanoparticles and/or in the emulsifier monolayer or the membrane layers.

8 Claims, No Drawings

COMPOSITIONS FOR THE TARGETTED RELEASE OF FRAGRANCES AND AROMAS

The invention relates to compositions for the targeted release of fragrances and aromas, specifically cosmetic, pharmaceutical, food or detergent compositions, and to the use of surfactants which form lyotropic lamellar liquid-crystalline phases as storage media for the targeted release of fragrances and aromas.

Many cosmetic, pharmaceutical, food or detergent compositions comprise fragrances, which should be understood as meaning both fragrant oils and also aroma substances. The fragrances are usually admixed into the compositions directly. This procedure has a number of disadvantages. Firstly, during use, it is barely possible to control the release of the fragrance, meaning that delayed release in particular is not possible. In addition, the fragrances are generally not protected against oxidative composition. For this reason, relatively large amounts of fragrances often have to be used in the compositions in order to achieve an adequate long-term effect and an adequate effect following prolonged storage.

On the other hand, fragrances are an important cost-determining constituent of, in particular, cosmetic compositions. If the effectiveness of the fragrances could be increased during use, it would be possible to make do with lesser amounts. In this case, cosmetic compositions could be prepared more cost-effectively.

The object of the present invention is to provide compositions for the targeted release of fragrances and aromas, in particular cosmetic, pharmaceutical, food or detergent compositions, which permit the use of small amounts of the fragrance and/or aroma, permit a targeted, for example delayed or cascaded, release of the fragrance and/or aroma and prevent oxidation of the fragrance and/or aroma.

The object is achieved by using a fragrance and/or aroma composition for the targeted release of fragrances and/or aromas in the form of a solid lipid nanoparticle (SLN) dispersion in which lipid-based nanoparticles are present which are stabilized by an emulsifier monolayer, one or more membrane layers or other auxiliaries. Depending on the composition, the fragrances/aromas are included in the solid particles and the emulsifier membranes surrounding the particles. The fragrances/aromas can also be present in the region of the hydrophobic radicals of emulsifiers or surfactants which comprise hydrophilic and hydrophobic radicals.

The nature and time of the release depend both on the distribution of the fragrance/aroma between solid lipid phase and the associated membrane layer, and also of the melting point of the lipid phase.

The object is also achieved by a fragrance or aroma composition for the targeted release of fragrances or aromas, comprising surfactants which have hydrophilic and hydrophobic radicals and are present in a lyotropic lamellar liquid-crystalline phase, the fragrances/aromas, depending on the solubility or structure, being included in the membranes/lamellae themselves or between these, or being incorporated in the region of the hydrophobic radicals of the surfactants.

The object is also achieved by fragrance and/or aroma composition for the targeted release of fragrances and/or aromas in the form of a PO (polyol-in-oil) emulsion or POW (polyol-in-oil-in-water) emulsion. The fragrance or the aroma here are completely encapsulated in the internal polyol phase, or are present in the region of the hydrophobic radicals of the emulsifiers or surfactants, the emulsion comprising emulsifiers or surfactants with hydrophilic and hydrophobic radicals.

According to the invention, the object is also achieved by using surfactants which form lyotropic lamellar liquid-crystalline phases as storage media for the targeted release of fragrances and aromas.

The composition can be used here for the targeted or controlled, for example cascaded or delayed, release of the fragrance and/or aroma following or during application in cosmetic, pharmaceutical, food or detergent compositions. Fragrances are used both in leave-on products, such as, for example, skincare products, and also in rinse-off products, such as shampoos, detergents. Since aroma substances used in foods only have a limited residence time in the oral cavity, they are included in the rinse-off products.

In the case of leave-on products, it is desirable to achieve as long-lasting a fragrance experience as possible. For this, the volatility of the fragrance has to be reduced. Furthermore, in the case of leave-on products, the formation of a fragrance pyramid is expected, i.e. a cascaded release of the fragrances present in the fragrance composition.

In the case of rinse-off products, two problems mostly arise. Firstly, the majority of the fragrance is removed again with the wash liquor from the surface to which it is to be applied. Secondly, the residual amount which remains evaporates relatively quickly. The composition according to the invention permits, as a result of surface-affinity modification of their composition, a greatly improved adhesion of the carrier and a very long fragrance release.

In addition, the compositions according to the invention prevent oxidation of the fragrances and/or aromas.

Preferably, the composition is in the form of a solid liquid nanoparticle (SLN) dispersion in which a lyotropic lamellar liquid-crystalline phase may be present in lipid-based particles, but does not have to be.

When used in SLN dispersions, the fragrance oil/aroma can be released in a controlled manner, for example in a cascaded manner, resulting in a long fragrance experience. These embodiments are particularly advantageous for leave-on products.

Pharmaceutical, cosmetic and/or food active ingredients are often encapsulated in solid active ingredient carriers, such as gelatin capsules, cyclodextrins, polymers etc. The active ingredient carrier here can be tailored to the particular application and permits a suitable dosage and release of the active ingredient. In the past, solid lipid nanoparticles, which are also referred to as SLN, have been developed. They represent an alternative carrier system to emulsions and liposomes. The nanoparticles can comprise hydrophilic or hydrophobic pharmaceutical active ingredients and can be administered orally or parenterally. For this, nanoparticles with an average particle diameter in the range from 50 nm to 1 µm are usually used. In contrast to the known emulsions, a solid lipid is used as matrix material. To ensure high bioacceptance and good in vivo degradability, predominantly physiologically compatible lipids or lipids composed of physiological components, such as glycosides from endogenous fatty acids are used. During the preparation, emulsifiers or surfactants are usually also used. The preparation usually takes place by high-pressure homogenization. In this, the lipid used as matrix is melted, and an active ingredient is dissolved or dispersed in the melt. Usually, the active ingredient-containing melt is dispersed with an aqueous surfactant solution at the same temperature with stirring. The dispersion obtained in this way is then homogenized in a high-pressure homogenizer, for example a piston-gap homogenizer at pressures in the range from 200 to 1500 bar in the hot state. This gives an emulsion whose lipid phase recrystallizes to give solid lipid nanoparticles upon cooling.

Alternatively, a cold homogenization can be carried out during which the active ingredient is in turn incorporated into a molten lipid phase. The mixed phase obtained is then cooled, and the solid is ground to a particle size in the range from 50 to 100 µm. The lipid particles obtained in this way are then dispersed in a cold surfactant solution, and the resulting dispersion is then high-pressure-homogenized.

The preparation of the SLN dispersion is also possible by
a) mixing the fragrance/aroma with the lipid-based active ingredient carrier and at least one emulsifier, which leads, in stage b), to the formation of a preferably lyotropic liquid-crystalline mixed phase, at a temperature above the melting or softening point of the active ingredient carrier, to form a phase B,
b) mechanical mixing of the phase B with an aqueous phase A which can comprise an emulsifier, at a temperature above the melting or softening point of the active ingredient carrier, where the weight ratio of phase B to phase A is 1:5 to 5:1, without high-pressure homogenization, to form a preferably lyotropic liquid-crystalline mixed phase,
c) dilution of the mixed phase with an aqueous phase which can comprise an emulsifier, at a temperature of the aqueous phase which is below the melting or softening point of the active ingredient carrier, for example at least 15° C. below, with stirring and without high-pressure homogenization, to a desired end concentration of the dispersion.

It has been found that aqueous active ingredient carrier dispersions in which solid lipid-based active ingredient carrier particles with an average diameter in the range from 10 to 1000 nm are present can be prepared advantageously if a lipid melt is mixed with an aqueous phase, heated to the same temperature, in a certain weight ratio of from 1:5 to 5:1. The mixing can be achieved here by customary mechanical stirrers which have the stirring power of a household mixer (or household kitchen stirrers). In laboratory operation it was, for example, possible to achieve an adequate stirring effect using a Braun® kitchen mixer which has a mixing bead in the form of a twin-paddle propeller with an overall diameter of 50 mm. The mixing propeller was surrounded by a protective ring with a diameter of 63 mm. The maximum power consumption of the kitchen mixer was 350 W. It was the model MR 550, type 4189.

The mechanical mixing in stage b) and the stirring in stage c) takes place preferably using stirrers which have a peripheral speed in the range from 1 to 20 m/s, particularly preferably 1 to 3 m/s.

Preferably, the shear action of the stirrer here corresponds to the shear action of a household kitchen stirrer or mixer, as is commercially available and has been described above.

The weight ratio of phase B to phase A in stage b) is preferably 1:2 to 2:1, particularly preferably 1:1.5 to 1.5:1.

In the text below, the active ingredient carriers suitable for SLN, suitable emulsifiers which preferably form lamellar structures, suitable pharmaceutical, cosmetic and food active ingredients and other possible ingredients of the aqueous active ingredient carrier dispersion are explained in more detail.

The active ingredient carrier particles used are preferably lipid-based particles. These include lipids and lipid-like structures. Examples of suitable lipids are the di- and triglycerides of the saturated straight-chain fatty acids having 12 to 30 carbon atoms, such as lauric acid, myristic acid, palmitic acid, stearic acid, arachidic acid, behenic acid, lignoceric acid, cerotinic acid, melesic acid and esters thereof with other saturated fatty alcohols having 4 to 22, preferably 12 to 22, carbon atoms, such as lauryl alcohol, myristyl alcohol, cetyl alcohol, stearyl alcohol, arachidyl alcohol, behenyl alcohol, saturated wax alcohols having 24 to 30 carbon atoms, such as lignoceryl alcohol, ceryl alcohol, cerotyl alcohol, myricyl alcohol. Preference is given to di-, triglycerides, fatty alcohols, esters or ethers thereof, waxes, lipid peptides or mixtures thereof. In particular, synthetic di- and triglycerides are used as individual substances or in the form of a mixture, for example in the form of a hard fat. Glycerol trifatty acid esters are, for example, glycerol trilaurate, glycerol trimyristate, glycerol tripalmitate, glycerol tristearate or glycerol tribehenate. Suitable waxes are, for example, cetyl palmitate and cera alba (bleached wax, DAB9).

The amount of the active ingredient carrier particles, based on the total aqueous active ingredient carrier dispersion, is preferably 0.1 to 30% by weight, particularly preferably 1 to 10% by weight. In addition to the lipids, dispersion stabilizers and emulsifiers can be used. They can be used, for example, in amounts of from 0.01 to 10% by weight, preferably 0.05 to 5% by weight. Examples of suitable substances are surfactants, in particular alkyl lactylates, such as stearoyl lactylate, isethionates, alkyl sulfates, such as cetyl sulfate, diamide ether sulfates, alkyl polyglycosides, phosphoric esters, taurates, sulfosuccinates, alkyl polyglycosides, phosphoric esters, taurates, sulfosuccinates, alkyl sarcosinates, such as sodium lauryl sarcosinate and alkyl glutamates, such as sodium lauryl glutamate, ethoxylated sorbitan fatty acid esters, block polymers and block copolymers (such as, for example, poloxamers and poloxamines), polyglycerol ethers and esters, lecithins of varying origin (for example egg or soya lecithin), chemically modified lecithins (for example hydrogenated lecithin) and also phospholipids and sphingolipids, mixtures of lecithins with phospholipids, sterols (for example cholesterol and cholesterol derivatives and stigmasterol), esters and ethers of sugars or sugar alcohols with fatty acids or fatty alcohols (for example sucrose monostearate), sterically stabilizing substances, such as poloxamers and polomaxines (polyoxyetlhylene-polyoxypropylene block polymers), ethoxylated sorbitan fatty acid esters, ethoxylated mono- and diglycerides, ethoxylated lipids and lipoids, ethoxylated fatty alcohols or fatty acids and charge stabilizers or charge carriers, such as, for example, dicetyl phosphate, phosphatidylglycerol, and saturated and unsaturated fatty acids, sodium cholate, sodium glycolcholate, sodium taurocholate or mixtures thereof, amino acids or peptizers, such as sodium citrate (see J. S. Lucks, B. W. Müller. R. H. Müller. Int. J. Pharmaceutics 63, pages 183 to 18 (1990)), viscosity-increasing substances, such as cellulose ethers and esters (for example methyl cellulose, hydroxyethyl cellulose, hydroxypropyl cellulose, sodium carboxymethyl cellulose), polyvinyl derivatives, such as polyvinyl alcohol, polyvinylpyrrolidone, polyvinyl acetate, alginates, polyacrylates (for example Carbopol), xanthans and pectins.

As aqueous phase A it is possible to use water, aqueous solutions or mixtures of water with water-miscible liquids such as glycerol or polyethylene glycol. Further additional components for the aqueous phase are, for example, mannose, glucose, fructose, xylose, trehalose, mannitol, sorbital, xylitol or other polyols, such as polyethylene glycol, and electrolytes such as sodium chloride. These additional components can be used in an amount of from 1 to 30% by weight, based on the aqueous phase A.

If desired, it is also possible to use viscosity-increasing substances or charge carriers as are described in EP-B-0 605 497. Thickeners which can be used are, for example, polysaccharides, polyalkyl acrylates, polyalkyl cyanoacrylates, polyalkylvinylpyrrolidones, acrylic polymers, polylactic acids or polylactides.

Lipids and emulsifiers are preferably used in a weight ratio of from 50:1 to 2:1, preferably 15:1 to 30:1. The amount of fragrance oil or aroma is preferably 0.1 to 30% by weight.

The average diameter of the active ingredient particles is preferably 50 to 1000 nm, particularly preferably 100 to 500 nm.

In the compositions, the water resistance and the ability to spread and adhere can be increased by adding silicone. Suitable silicone derivatives here are dimethicone, alkyl- and aryl-substituted silicones, amino-substituted silicone oils, silicone copolyols with alkyl polyglycosides, modified silicone oils etc. Alternatively or additionally, fluorinated hydrocarbons can also be used.

In SLN dispersions, the release behavior is dependent on the melting point of the lipid particles. In addition, the release behavior is dependent on the composition and amount of the emulsifier used.

According to one embodiment of the invention, lipid-based particles with varying melting points are present in the SLN dispersions. As a result, a targeted release, in particular cascaded release, of the fragrance oils and aromas present is possible. Firstly, the lipid particles with the lowest melting point soften and release the corresponding active ingredient. Only at a later time do the lipid particles with a higher melting point soften. Oil-soluble and/or amphiphilic fragrance oils or aromas are preferably stored in the lipid particles whereas water-soluble fragrances are incorporated into the aqueous phase. Upon using such a SLN dispersion, the fragrance oils and aromas present in the water are released first, whereas the fragrance oils and aroma substances present in the lipid particles are only released subsequently.

For the further cascaded release, the SLN dispersions can also be combined with the compositions described below, for example with PO or POW emulsions.

According to the invention, it has additionally been found that fragrances and aromas can be bound into liquid-crystalline lamellae which are formed by surfactants as lyotropic liquid-crystal phase, and in this form constitute a depot.

By virtue of the surfactants, a unilamellar or multilamellar system or a lyotropic liquid-crystalline mixed phase can be formed. The compositions according to the invention preferably have microscopically birefractive interfaces which are derived from a bilayer or a multilayer of the lamellar structures or LC phase surfactant.

According to the invention, the surfactants used are those which have hydrophilic and hydrophobic radicals and are able to form lyotropic lamellar liquid-crystalline phases. The formation of liquid-crystalline structures depends essentially on the geometry of the surfactants. Here, the ratio of hydrophilic to hydrophobic radical plays an important role. Surfactants with a space-filling hydrophilic group and a small hydrophobic radical often form micelles. However, micelles are in a dynamic equilibrium and continuously break down and form again. For this reason, micelles are not suitable as storage media for other ingredients. As the hydrophilic radical becomes smaller, the surfactants form rod-like micelles, vesicle double layers and sandwich double layers. According to the invention, surfactants are then used which can be present in a lyotropic lamellar liquid-crystalline phase. In the lyotropic state, fragrances are stored between the hydrophilic radicals or heads of the surfactants. The hydrophilic part of the surfactant can be varied depending on the desired adhesion to a subsequent substrate. For example, the hydrophobic part can be varied for adhesion to the human skin or to textile fibers.

Suitable surfactants which form lyotropic lamellar liquid-crystalline phases are know to the person skilled in the art. Natural or synthetic products can be used. The use of surfactant mixtures is also possible. Examples of suitable surfactants are the physiological bile salts, such as sodium cholate, sodium dehydrocholate, sodium deoxucholate, sodium glycolcholate, sodium taurocholate. Animal and vegetable phospholipids such as lecithins with their hydrogenated forms, and polypeptides such as gelatin with their modified forms, can likewise be used.

Suitable synthetic interface-active substances are the salts of the sulfosuccinic esters, polyoxyethylene acid betaine esters, acid betaine esters and sorbitan ethers, polyoxyethylene fatty alcohol ethers, polyoxyethylene stearic esters, and corresponding cocondensates of polyoxyethylene ethers with polyoxypropylene ethers, ethoxylated saturated glycerides, partial fatty acid glycerides and polyglycides. Examples of suitable surfactants are Biobase® EP and Ceralution® H.

Examples of suitable surfactants are also glycerol esters, polyglycerol esters, sorbitan esters, sorbitol esters, fatty alcohols, propylene glycol esters, alkyl glucoside esters, sugar esters, lecithin, silicone copolymers, wool wax and mixtures thereof or derivatives thereof. Glycerol esters, polyglycerol esters, alkoxylates and fatty alcohols, and isoalcohols can be derived, for example, from ricinus fatty acid, 12-hydroxstearic acid, isostearic acid, oleic acid, linoleic acid, linolenic acid, stearic acid, myristic acid, lauric acid and capric acid. Besides the specified esters, succinates, amides or ethanolamides of the fatty acids may also be present. Suitable fatty acid alkoxylates are, in particular, the ethoxylates, propoxylates or mixed ethoxylates/propoxylates.

The surfactants can be selected depending on the chosen field of use. For the use in the detergents sector, for example, preference is given to using cationic surfactants. For compositions to be applied to human skin, particularly lactylates, glutamates, diamide ether sulfates, ethoxylates of alcohols or glycols, betaines, amphiphilic coemulsifiers, such as sorbitan monostearate and fatty alcohols, fatty acid condensates, sarcosinates, protein fatty acid condensates, sulfosuccinates and ether carboxylates are used.

Depending on the shape and size of the formed lamellae, the compositions can appear clear or exhibit a pearl effect. Particles with an average particle size in the region of 100 nm appear clear, whereas long lamellae usually exhibit a pearl effect.

The lyotropic lamellar liquid-crystalline phase here is preferably formed using water, alcohols, polyols or mixtures thereof. The hydrophilic parts of the surfactants orientate themselves to the water, alcohol, polyol phase or mixed phase thereof, while the hydrophobic parts in the lamellar structure point to one another. In this arrangement, the fragrances or aromas are then incorporated and stored into the spaces between the hydrophobic radicals and/or of the surfactants. The amount of storable fragrance depends here on the nature of the surfactant used and on the structure of the liquid-crystalline phase. As a rule, surfactant and fragrance or aroma are present in a weight ratio from 1:100 to 100:1, preferably 1:20 to 20:1, particularly preferably 1:5 to 5:1.

The release behavior of the fragrances/aromas from the liquid-crystalline phases depends on the melting point of the lamellar structure and the type of hydrophobic radical in the surfactant. If polyols are used instead of water to form the liquid-crystalline phase, the volatility and availability can be reduced, giving a longer-lasting storage effect. In the case of rinse-off products, such as detergents, shampoos, shower gels or soaps, the majority of the composition is rinsed off and removed from the substrate. The compositions according to the invention allow the attachment of the fragrances and aromas to the substrate, for example the skin or textiles, meaning that a relatively large amount of fragrance remains on the substrate.

A cascaded release can be important especially also in the case of leave-on products if different fragrance oils or aroma substances are released at different times. In each case, a new stimulus is thus exerted on the sensory organs, meaning that the perception is increased. If only one stimulus is present, a saturation usually occurs which adversely affects the perception of the fragrance oil or aroma. With the help of the compositions according to the invention, the odor and/or taste sensation continues.

The varying compositions such as emulsions, dispersions or SLN dispersions can also be mixed or combined in order to obtain new property profiles from the combination.

Particularly SLN dispersions or lipid particles lead to optimum oxidation protection for the fragrances and aromas since the fragrances and aromas are present in embedded form within the solid and are thus sealed against the entry of air. If appropriate, amphiphilic agents and antioxidants can also be used in the compositions in order to further increase the oxidation stability.

According to the invention, fragrances and aromas are understood as meaning both fragrance oils (fragrance) and also aroma substances (flavor). These are odorants, specifically fragrances. Basic substances of the fragrances are generally essential oils, flower oils, extracts from plant and animal drugs, odorants isolated from natural products, chemically modified (semisynthetic) odorants, and odorants obtained by purely synthetic means. According to the invention, the fragrances also include flavorings.

The fragrances and aromas can here originate from a large number of plant starting materials. For example, mention may be made of: flowers, for example from lavender, rose, jasmine, neroli; stems and leaves, for example from geranium, patchouli, petitgrain, fruits, such as anise, coriander, caraway, juniper; fruit peels, for example from citrus fruits, such as bergamots, lemons, oranges; seeds, such as mace, angelica, celery, cardamom; roots, such as angelica, cosus, iris, calmus; wood, such as sandalwood, guaiacwood, cedarwood, rosewood; herbs and grasses, such as tarragon, lemongrass, sage, thyme; needles and branches, for example from spruces, firs, pines, dwarf-pines; resins and balsams, for example from galvanum, elemi, benzoin, myrrh, olibanum, opoponax.

Animal raw materials are, for example, ambergris, musk, civet, castoreum.

Examples of semisynthetic odorants are isoeugenol, vanillin, hydroxycitronellal, citronellol, geranyl acetate, ionone and methylionones. The completely synthetic odorants or fragrances are very diverse and often orientate themselves to natural substances. For a description of the fragrances, reference may be made, for example, to Römpp, Chemielexikon, 9th edition, keywords "Parfums [perfumes]", "Riechstoffe [odorants]", "Duftstoffe [fragrances]". Further suitable fragrances and aromas are known to the person skilled in the art.

Besides fragrances and aromas, further active ingredients can also be incorporated into the liquid-crystalline phases. In the case of cosmetics, these are, in particular, cosmetic or pharmaceutical active ingredients, for example antioxidants, and, in the case of detergent compositions, are for example, additives such as fabric softener active components.

The liquid-crystalline phase is formed, for example, using water, ether alcohols, ether polyols, ester polyols, aminofunctional polyols or mixtures thereof.

The ether alcohol preferably has the general formula (1) below.

$$R^1\text{—O-[EO—]}_n\text{[PO—]}_m R^2 \qquad (I)$$

where
$R^1$ is $C_{1-4}$-alkyl,
$R^2$ is hydrogen or $C_{1-4}$-alkyl,
n is on average 1 to 100,
m is on average 0 to n/2
EO, PO are basic building blocks derived from ethylene oxide and propylene oxide, which may be in any order if both basic building blocks are present.

In the ether alcohols of the general formula (I) it is possible for basic building blocks derived from ethylene oxide and, if appropriate, additionally from propylene oxide to be present. These basic building blocks have the structures —CH$_2$—CH$_2$—O—, —CH$_2$—CH(CH$_3$)—O— and —CH(CH$_3$)—CH$_2$—O—. If the two basic building blocks derived from ethylene oxide and propylene oxide are present, they may be in any order. This means that in each case one or more blocks derived from ethylene oxide and propylene oxide can be joined together. In addition, the units derived from ethylene oxide and propylene oxide can also be present alternately or randomly. The possible continuous transitions between these forms are likewise possible according to the invention.

In the general formula (I), the proportion of the basic building blocks derived from propylene oxide is at most a fraction of the amount of basic building blocks derived from ethylene oxide. While on average 1 to 100, preferably 2 to 70, particularly preferably 3 to 50, in particular 5 to 15, basic building blocks derived from ethylene oxide are present, 0 to n/2, preferably 0 to n/4, particularly preferably 0 to n/8, basic building blocks derived from propylene oxide are present on average. If basic building blocks derived from propylene oxide are present, their amount is preferably n/10 to n/4, particularly preferably n/8 to n/5. The numbers n and m are average values since a distribution of the degree of alkoxylation generally arises during the alkoxylation. For this reason, odd-numbered values for n and m are also possible. The width of the distribution of the degree of alkoxylation depends, inter alia, also on the alkoxylation catalyst used. It is also possible to establish discrete degrees of alkoxylation or very narrow distributions of the degree of alkoxylation.

$R^1$ is a $C_{1-4}$-alkyl radical, preferably $C_{1-3}$-alkyl radical, particularly preferably $C_{1-2}$-alkyl radical, in particular a methyl radical. Propyl radicals comprise n-propyl and isopropyl, while butyl radicals comprise n-butyl, isobutyl, tert-butyl.

$R^2$ is hydrogen or a radical as defined above for $R^1$. The meaning of $R^2$ is independent of the meaning of the radical $R^1$. $R^2$ is particularly preferably hydrogen. The expression "ether alcohol" used in the description and the claims comprises all compounds of the general formula (I), i.e, also the cases in which $R^2$ is not a hydrogen atom and thus no free hydroxyl groups are present in the molecule.

The ether alcohol is preferably a methanol ethoxyl ate having 5 to 15 ethylene oxide units.

Specific preference is given to using polyethylene glycol monomethyl ether (12 EO) and polyethylene glycol monomethyl ether (7 EO). These are pure methyl alcohol ethoxylates. Such compounds are known per se and have hitherto been used for the preparation of terminally methyl-capped fatty acid polyethylene glycol esters. The compounds are commercially available.

The polyols used may be the customary known polyols, such as propylene glycol, butylene glycol, ethylene glycol, polyalkylene glycol, glycerol, polyglycerol, glycosides, sorbitol, mannitol, pentaerythritol, trimethylolpropane or mixtures thereof. Suitable polyalkylene glycols are, in particular, polyethylene glycol and polypropylene glycol. Further suitable polyols are known to the person skilled in the art, for example aromatic polyols such as emodin/aloe vera.

Suitable ester polyols are derived from glycerol, $C_{2-20}$-alkylene glycol, preferably $C_{2-10}$-alkylene glycol, in particular $C_{2-8}$-alkylene glycol, for example propylene glycol, butylene glycol and specifically ethylene glycol, poly($C_{2-20}$-alkylene) glycol preferably poly($C_{2-10}$-alkylene) glycol, in particular poly($C_{2-8}$-alkylene) glycol with one or more different alkylene radicals, for example polyethylene glycol, in which up to 30% of the ethyleneoxy units may be replaced by propyleneoxy units, polyglycerols, sorbitol, pentaerythritol as polyol component and aliphatic $C_{3-6}$ carboxylic acids which, besides a carboxyl group, have at least one further functional group chosen from hydroxyl and carboxyl groups, as acid component.

The ester polyols which can be used according to the invention are derived from the polyol components and acid components which are esterified with one another. In the polyethylene glycol, preferably 1 to 600, particularly preferably 1 to 100, ethyleneoxy units are present.

Preferably, the carboxylic acids comprise only carbon, hydrogen and oxygen as atoms. The carbon chain here may be free from double bonds or comprise one double bond. Examples of suitable acid components are lactic acid, maleic acid, tartaric acid and citric acid.

In the ester polyols, one, two, three or more hydroxyl groups, for example all of the hydroxyl, groups, of the polyol component may be in esterified form. Similarly, one, two, several or all of the carboxyl groups of the acid component may be present in ester form.

The ester polyols used according to the invention can, at room temperature (25° C.), be in solid form, glass-like form, viscous form or liquid form. By mixing several ester polyols it is possible to adjust the properties in a targeted manner. For example, lactates are usually in liquid form whereas citrates are in a glass-like state and only become viscous at a temperature of about 50° C. A mixture of citrate and lactate in the ratio 1:1 is glass-like. A mixture of citrate and lactate in the weight ratio 1:2 by contrast, is viscous. At room temperature, the ester polyols are often glass-clear and solid.

The ester polyols can be used in combination with amino-functional polyols, ether alcohols or both compounds. The proportion of the ester polyols in such mixtures is preferably at least 10% by weight, particularly preferably at least 15% by weight, in particular at least 20% by weight.

As amino-functional polyol it is possible to use any suitable amino-functional polyol which has a melting point of less than 100° C., preferably of less than 50° C. The expression "amino-functional" polyols means that at least one amine group or amide group is present in the polyol. The polyol additionally has at least two hydroxyl groups. It may be an aliphatic, aromatic or aromatic/aliphatic polyol. It is preferably an aliphatic polyol, 2 to 10, particularly preferably 2 to 5, in particular to 2 to 3, hydroxyl groups are particularly preferably present in the polyol, Over and above the specified functional groups, the amino-functional polyols can have carbonyl groups, carboxyl groups, thiol groups and carbon-carbon double bonds or triple bonds. They can also have ether groups. Some of the hydroxyl groups present in the molecule can be etherified with the proviso that at least two free hydroxyl groups are present in the molecule. The amino-functional polyols used according to the invention preferably comprise one or two amide groups.

According to the invention, preference is given to using amino-functional polyols which have two or three hydroxyl groups and one or two amide groups. They can also have an additional thiol group or carboxyl group. Preferably, the compounds comprise 5 to 15 carbon atoms, particularly preferably 7 to 12 carbon atoms.

The amino-functional polyol is preferably a pantothene derivative of the general formula (II)

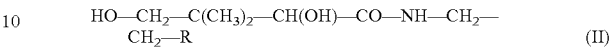

$$HO-CH_2-C(CH_3)_2-CH(OH)-CO-NH-CH_2-CH_2-R \qquad (II)$$

where R is $COOR^1$, $CH_2-OR^1$, $CO-NH-CH_2-CH_2-SR^1$
$R^1$ is H, $C_{1-12}$-alkyl, phenyl.

R is preferably a radical $CH_2-OR^1$, $R^1$ is preferably hydrogen or $C_{1-6}$-alkyl, in particular hydrogen or $C_{1-3}$-alkyl.

Particular preference is given to using pantothenic acid, panthenol or pantheteine. The pantothene derivatives are preferably in the (R) form. Pantothenic acid can also be used in the form of the salts, preference specifically being given to the pantothene derivative (R)-panthenol.

The compounds preferably used according to the invention have a molecular fragment derived from pantoic acid, and a molecular fragment derived from β-alanine provided it is a pantothenic acid-comparable compound.

Panthenol and pantothenic acid are known from the medical field for wound healing, and also from hair-treatment compositions and animal feed additives. The preparation can take place via a biosynthesis from 2-oxo-3-methylbutanoic acid or from pantolactone. Further preparation processes are generally known. Reference may also be made to Beilstein EIV 4, 2571, Bellstein EV 18/1, 22 and Beilstein E IV 4, 2569f and Isler et al., Vitamins II, pages 309 to 339, Thieme-Verlag, Stuttgart, 1988. There is also extensive patent literature which deals with the use of pantothene derivatives, in particular of panthenol in cosmetic and pharmaceutical compositions.

Preferably, in the fragrance depots according to the invention, 1 to 95% by weight, particularly preferably 10 to 50% by weight, of water, alcohols, polyols or mixtures thereof, 0.5 to 30% by weight, particularly preferably 2 to 20% by weight, of surfactants and 0.1 to 60% by weight, particularly preferably 2 to 30% by weight, of fragrances and/or aromas are present, based on the total weight of the composition, which gives 100% by weight. Besides the fragrances and aromas, surfactants and the water, alcohol or polyol phase, the fragrance depot or the composition can also comprise further customary ingredients. It can, however, also consist of the three specified components in the amounts stated.

The compositions according to the invention are prepared by mixing the surfactant with the water, alcohol, polyol or mixture thereof, which is in liquid form, to form a lyotropic lamellar liquid-crystalline phase, and then mixing in the fragrance and/or aroma. According to the invention, at least 80%, preferably at least 90%, in particular at least 95%, preferably the entire amount of the fragrance and/or aroma is incorporated into the liquid-crystalline structure, so that the fragrances and/or aromas are present in stored form in the hydrophobic parts of the surfactants. As described, the appearance of the fragrance/aroma depot can be controlled, meaning that the depot can appear clear or with an effect such as a pearl effect.

According to the invention there are no fragrance/aroma droplets present in the compositions, and neither is there a fragrance/aroma emulsion present. The fragrance/aroma is deposited at an interface in the LC structures with the highest absorbancy.

The composition according to the invention can be used for the delayed release of the fragrance/aroma in cosmetic, pharmaceutical, food or detergent compositions. The cosmetic and pharmaceutical compositions may be, for example, rinse-off products or leave-on products. The rinse-off products are, in particular, products for cleansing the hair and skin, such as soaps, shampoos, shower oils, shower baths or bath additives. Leave-on products are products which are applied to the skin and are intended to remain on the skin. These are, in particular, gels, creams, lotions such as photoprotective compositions, in particular sun creams, moisturizing creams and other such products.

Upon applying the composition to the skin, the water or polyol evaporates, and the LC structures are spread on the skin. The release behavior is here is dependent on the melting point of the lamellae and the type of hydrophobic radical in the surfactants. The release behavior can thus be controlled within wide limits. This results in a greater availability of the fragrance and/or aroma on the skin compared with compositions and application mechanisms for fragrances/aromas used to date. Due to the large fraction of attaching fragrance/aroma, only small amounts of the fragrance need to be used. A targeted release on the skin is possible by combining floater with polyols. The spreading and fixing can be tailored to the requirements in a suitable manner.

Over and above the storage effect, the procedure according to the invention permits extensive protection of the fragrances against oxidative decomposition. If appropriate, further antioxidants can also be added. Even without the addition of antioxidants, the fragrance/aroma in the depots according to the invention is considerably better protected against oxidation than in conventional application forms.

The invention also provides cosmetic, pharmaceutical, food or detergent compositions which comprise a composition as described. The compositions can, for example, be in the form of an emulsion or dispersion. Here, they can be in the form of any desired emulsions, multiple emulsions, vesicles or dispersions. They are preferably in the form of a PO emulsion or POW emulsion. Mixtures of the emulsions and dispersions are also possible.

In polyol-in-oil emulsions (PO emulsions), one or more polyol phases may be present. The polyol phase here is preferably not miscible with oil. Oils which can be used in the oil phase are all known suitable oils and mixtures thereof. Examples of suitable oils are silicone oils and derivatives thereof which may be linear or cyclic, natural ester oils, such as grapeseed oil, olive oil or sunflower oil, synthetic ester oils, such as neutral oils, which may be linear or branched, paraffin oil and isoparaffin oils, ester oils, for example of citrates, lactates, aleates, salicylates, cinnamates or camphor derivatives triglycerides, fatty alcohols or mixtures thereof.

In the PO emulsions, the weight ratio of polyol phase to oil phase is preferably 10:90 to 90:10, particularly preferably 25:75 to 75:25 and in particular 40:60 to 60:40.

To form the PO emulsions, the emulsifiers specified above can be used.

The amount of emulsifier can be tailored to the practical requirements. Preferably, the emulsifier is used in an amount of from 0.1 to 20% by weight, particularly preferably 0.5 to 15% by weight, in particular 1 to 8% by weight, based on the total P/O emulsion. In some cases, concentrations deviating from this may be required.

According to one embodiment of the invention, the polyol phase can comprise a cosmetic and/or pharmaceutical active ingredient dissolved in the phase. It may also be a detergent, food or agricultural active ingredient.

The active ingredients are preferably organic compounds which are insoluble or insufficiently soluble in lipophilic and hydrophilic media. The compounds here are in particular insoluble or insufficiently soluble in water and oil. Any suitable active ingredients can be used provided they dissolve in the amino-functional polyol or the polyol phase which comprises the amino-functional polyol. Suitable active ingredients are, for example, dichlorphenac, ibuprofen, acetylsalicylic acid, erythromycin, ketoprofen, cortisone, glutocorticoids.

Also of suitability are cosmetic active ingredients which are particularly sensitive to oxidation or hydrolysis, such as, for example, polyphenols. Mention may be made here of catechins (such as epicatechin, epicatechin-3-gallate, epigallocatechin, epigallocatechin-3-gallate), flavonoids (such as luteolin, apigenin, rutin, quercitin, fisetin, kaempherol, rhametin), isoflavones (such as genistein, daidzein, glycitein, prunetin), coumarins (such as daphnetin, umbelliferone), emodin, resveratrol, oregonin.

Vitamins such as retinol, tocopherol, ascorbic acid, riboflavin, pyridoxin are suitable.

Also suitable are whole extracts from plants which comprise, inter alia, the above molecules or classes of molecules.

The P/O emulsion described above can also be emulsified in water or a water-in-oil emulsion. This results in a polyol-in-oil-in-water emulsion (P/O/W emulsion) which comprises at least one emulsion as described above and additionally at least one aqueous phase. Such multiple emulsions can correspond in terms of structure to the emulsions described in DE-A-43 41 113, the polyol component being varied in a manner according to the invention. The structure of the polyol-in-oil emulsion can correspond to the structure of the emulsions described in DE-A-43 41 114, the polyol phase according to the invention being used as polyol phase.

When incorporating the P/O emulsion according to the invention into water or aqueous systems, the weight ratio of the individual phases can be varied within wide ranges. Preferably, in the ultimately obtained P/O/W emulsion, the weight fraction of the P/O emulsion is 0.01 to 80% by weight, particularly preferably 0.1 to 70% by weight, in particular 1 to 30% by weight, based on the total P/O/W emulsion.

When incorporating the P/O emulsion according to the invention into an O/W emulsion, the fraction of the P/O emulsion is preferably 0.01 to 60% by weight, particularly preferably 0.1 to 40% by weight, in particular 1 to 30% by weight, based on the ultimately obtained P/O/W emulsion. In the O/W emulsion which is used for this purpose, the oil fraction is preferably 1 to 80% by weight, particularly preferably 1 to 30% by weight, based on the O/W emulsion used.

The individual phases of the emulsions can also have customary ingredients known for the individual phases. For example, the individual phases can comprise further pharmaceutical or cosmetic, detergent, food or agricultural active ingredients which are soluble in these phases. The aqueous phase can, for example, comprise organic soluble photoprotective filters, hydrophilically coated micropigment, electrolytes, alcohols etc. Some or all of the phases can additionally comprise solids, which are preferably chosen from pigments, microspheres, silica gel and similar substances. The oil phase can, for example, comprise organically modified clay minerals, hydrophobically coated pigments, organic oil-soluble photoprotective filters, oil-soluble cosmetic active ingredients, waxes, metal soaps, such as magnesium stearate. Vaseline or mixtures thereof. Pigments which can be specified are titanium dioxide, zinc oxide and barium sulfate. In particular, titanium dioxide or zinc oxide are customary in cosmetics as photoprotective filters and can be applied to the skin in a particularly smooth and even manner using the emulsions according to the invention. Microspheres or silica gel can be used as carriers for active ingredients, and waxes can be used, for example, as basis for polishes.

Moreover, the water phase can comprise glycerol, polyethylene glycol, propylene glycol, ethylene glycol and similar compounds, and derivatives thereof. The use of customary auxiliaries and additives in the emulsions is known to the person skilled in the art.

The P/O emulsions can be prepared by known methods, as are described, for example, in DE-A-43 41 114 and DE-A-43 41 113. For the preparation, the polyol phase and the oil phase, each of which can comprise emulsifier, are usually heated separately to a temperature in the range from 20 to 90° C. and then combined with stirring.

Depending on the composition, on the phase volume ratio and any solids fraction present, the emulsions may be prepared and be present in the form of solid or free-flowing emulsions. These are very stable emulsions which have a high long-term stability under normal handling conditions. In particular, they satisfy the usual stability requirements within the temperature range from −5° C. to +45° C. The droplets present in the emulsion here are very stable, for which reason the emulsions are particularly suitable as carriers for many types of active ingredients.

The emulsions prepared using the specified emulsifiers can be obtained by a simple mixing operation with stirring, the stability of the emulsions usually being barely influenced, if at all, by the stirrer energy input and the type of stirrer. To prepare the emulsion according to the invention, any suitable standard commercial stirrer can be used.

The emulsions according to the invention are preferably used in cosmetic and/or pharmaceutical compositions or else in detergent, food or agricultural compositions. The invention thus also provides such cosmetic and/or pharmaceutical compositions which comprise at least one of the specified emulsions. The cosmetic and/or pharmaceutical compositions may be hand or body lotions, oils, ointments, pastes, gels, lip care products, face care products and similar compositions. The compositions can be used in solid, liquid or aerosol form.

In combination with water or polyols, rinse-off and leave-on products can be obtained. The fragrances are often polyol-soluble. In a POW emulsion, skin-affinity polyols with the fragrance/aroma depot according to the invention and, if appropriate, antioxidants can bring about a delayed release of the perfume/aroma on the skin. As a result of the delayed release, a longer odor experience of the compositions according to the invention is possible. If, in contrast to this, a fragrance oil is applied as emulsion directly to the skin, it results in film formation and thus to a very rapid release, meaning that only a short odor experience is achieved.

In addition, the invention provides a method of preparing a multiple dispersion by mixing a dispersion which has been prepared as described above with another polyol phase or oil phase. The invention also provides a correspondingly prepared multiple dispersion. Multiple emulsions are described, for example, in DE-A-43 41 113.

Further ingredients of the aqueous active ingredient carrier dispersions prepared according to the invention are described in EP-B-0 605 497, EP-B-0 167 825 and U.S. Pat. No. 5,885,486.

In particular, for suitable stabilizing substances and charge stabilizers, reference is made to EP-B-0 605 497.

The invention will be illustrated in more detail by the examples below:

EXAMPLES a) P/O for P/O/W Washing Emulsion

| Trade name | CTFA/INCI | PO-1-1/0 [% by wt.] | PO-2-1/0 [% by wt.] |
| --- | --- | --- | --- |
| Phase A | | bt | bt |
| Dow Corning DC 5225 Formation Aid | Cyclomethicone, dimethicone copolyol | 40.00 | 40.00 |
| Phase B | | | |
| Propylene glycol | Propylene glycol | 48.00 | 48.00 |
| FRAG 261346 "sunrise" | Fragrance | 12.00 | 0.00 |
| Chlorealis | Fragrance (Drogoco) | 0.00 | 12.00 |
| Total: | | 100.00 | 100.00 |
| pH | | | |

The preparation is carried out by introducing phase B into phase A at room temperature. It is homogenized for two minutes.

b) P/O/W Washing Emulsion

| Trade name | CTFA/INCI | PO-1-1/0 [% by wt.] | PO-2-1/0 [% by wt.] |
| --- | --- | --- | --- |
| Phase A | | bt | bt |
| Texapon NSO | Sodium lauryl ether (2) sulfate | 10.00 | 10.00 |
| Keltrol | Xanthan gum | 0.50 | 0.50 |
| demin. water | Aqua | 84.50 | 84.50 |
| Phase B | | | |
| PO-1-1/0 | | 5.00 | 0.00 |
| PO-2-1/0 | | 0.00 | 5.00 |
| Total | | 100.00 | 100.00 |

The preparation is carried out by introducing phase B into phase A and subsequent stirring using a spatula.

The stability of the POW washing emulsion is at least 2 months at 40° C. The emulsion survives 5 thaw-freeze cycles.

c) Solid Lipid Nanoparticle with Encapsulated Fragrance Oil

| Trade name | Manufacturer | CTFA/INCI | SLN-2-2/0 [% by wt.] |
|---|---|---|---|
| Phase A | | | |
| demin. Water | — | Aqua | 15.00 |
| Keltrol | Kelco | Xanthan gum | 0.40 |
| Phase B | | | |
| Cetiol MM pastilles | Cognis | Myristyl myristate | 20.00 |
| Fragrance Design 72515J | Shaw Mudge | Fragrance | 10.0 |
| Pationic 138 A | RITA | Sodium lauroyl lactylate | 0.50 |
| Vitamin E | | d,l-a-Tocopherol | 1.00 |
| Ceralution H | Sasol | Behenyl alcohol, glyceryl stearate, glyc | 1.25 |
| Vitamin C Dipalmitate | Nikkol | Ascorbyl dipalmitate | 1.00 |
| Phase C | | | |
| demin. Water | — | Aqua | 50.2 |
| Phase D | | | |
| Phenonip | Nipa | Phenoxyethanol methylparaben, ethyl | 0.60 |
| Total: | | | 100.0 |
| Particle size distribution after the preparation | | | |
| Median [μm] | | | 0.42 |
| >1 μm [%] | | | 100 |
| $cm^2/cm^3$ | | | 140670 |

The preparation is carried out by heating the phases B (without fragrances) and phase A to 70° C. The fragrance is then introduced into phase B, phase B is slowly added to phase A, and the mixture is homogenized. The phase AB is then diluted with phase C at 60° C. and homogenized again. Finally, phase D is added.

The stability of the SLN dispersion is more than 7 weeks at 40° C. The emulsion survives more than 5 thaw-freeze cycles.

d) Pearlescent Washing Gel with Encapsulated Fragrance Oil

| Trade name | Manufacturer | CTFA/INCI | PG-3-1/0 [% by wt.] | PG-4-1/0 [% by wt.] | PG-5-1/0 [% by wt.] |
|---|---|---|---|---|---|
| demin. water | — | Aqua | 44.00 | 30.30 | 33.50 |
| Ceralution F | Sasol | Sodium lauroyl lactylate, sodium dicocoy | 10.00 | 0.00 | 0.00 |
| Pationic 138 A | RITA | Sodium lauroyl lactylate | 0.00 | 5.00 | 5.00 |
| Protelan AGL 95 | Zschimmerer & Sc | Sodium lauroyl glutamate | 0.00 | 0.00 | 13.50 |
| Protelan LS 9011 | Zschimmerer & Sc | Sodium lauroyl sarcosinate | 0.00 | 16.70 | 0.00 |
| Tegin D 1102 | Goldschmidt | PEG-3 stearate | 10.00 | 10.00 | 10.00 |
| Atlas G 4829 | Uniqema | Laureth-9 | 18.00 | 18.00 | 18.00 |
| Glycerol lactate | Sasol | Glycerol lactate | 8.00 | 8.00 | 8.00 |
| Fragrance Design 72515J | Shaw Mudge | Fragrance | 10.00 | 10.00 | 10.00 |
| Vitamin C Dipalmitate | Jan Dekker | Ascorbyl dipalmitate | 0.00 | 1.00 | 1.00 |
| Vitamin E | Roche | d,l-a-Tocopherol | 0.00 | 1.00 | 1.00 |
| Total | | | 100.0 | 100.0 | 100.0 |

The preparation takes place by melting the ingredients at temperatures of from 60 to 70° C. After mixing the molten ingredients, the fragrance oil is introduced, and the mixture is cooled to room temperature with stirring.

The pearlescent washing gels had a stability, of more than 7 weeks at 40° C. The washing gel survived more than 5 thaw-freeze cycles.

e) Washing Gel with Pearlescence

| Trade name | Manufacturer | CTFA/INCI | REFGEL [% by wt.] | PG-3-2/0 [% by wt.] | PG-5-2/0 [% by wt.] | PG-6-2/0 [% by wt.] |
|---|---|---|---|---|---|---|
| Phase A | | | | | | |
| Texapon NSO | Cognis | Sodium lauryl ether (2) sulfate | 30.00 | 30.00 | 30.00 | 30.00 |
| Fragrance Design 72515J | Shaw Mudge | Fragrance | 1.00 | 0.00 | 0.00 | 0.00 |
| demin. water | | | 65.50 | 56.50 | 56.50 | 56.50 |
| NaCl | Merck | Sodium chloride | 3.50 | 3.50 | 3.50 | 3.50 |
| Phase B | | | | | | |
| PG-3-1/0 | Shaw Mudge | Fragrance | 0.00 | 10.00 | 0.00 | 0.00 |
| PG-4-1/0 | | | 0.00 | 0.00 | 10.00 | 0.00 |
| PG-5-1/0 | | | 0.00 | 0.00 | 0.00 | 10.00 |
| Total | | | 100.00 | 100.00 | 100.00 | 100.00 |

The preparation takes place by diluting the ingredients of phase A at room temperature, adding the phase B and moderate homogenization.

Headspace chromatograms were created from the compositions; these monitor the development of fragrance components over a period in the gas phase.

The washing gels from example e) were applied to the human skin. For this, a headspace chromatogram (gas chromatogram) was firstly created directly following application. Relatively similar signals were produced for all of the gels. All of the ingredients of the fragrance oil composition appeared.

After washing the washing gel off the skin, considerably smaller signals were produced in the headspace chromatogram. For the washing gels WG-320, WG-520 and WG-620 the signals were stronger than for the reference washing gel. This indicates a larger amount of the fragrance oil remaining on the skin.

After a waiting time of one hour after the washing-off, a headspace chromatogram weas again recorded for all of the skin surfaces which had been treated with the various washing gels. For the washing gels according to the invention, the signals produced were considerably stronger, particular for hexyl acetate and limonan, compared to the reference gel. In the region of phenoxyethyl isobutyrate as well, considerably stronger signals were also produced for the washing gels according to the invention. From this it becomes clear that the washing gels according to the invention or the fragrance oils present therein attach better to the skin and bring about a delayed release. As a result, the fragrance experience when using the washing gels according to the invention lasts considerably longer than when using the reference washing gel.

The invention claimed is:

1. A method of preparing a solid lipid nanoparticle (SLN) dispersion for the targeted release of fragrances and/or aromas, the method comprising the steps of:
   a) mixing the fragrance and/or aroma with the lipid-based active ingredient carrier and at least one emulsifier, which leads, in stage b), to the formation of a lyotropic lamellar liquid-crystalline mixed phase, at a temperature above the melting or softening point of the active ingredient carrier, to form a phase B,
   b) mechanical mixing, without high-pressure homogenization, of the phase B with an aqueous phase or polyol phase A at a temperature that is above the melting or softening point of the active ingredient carrier and is up to 70 degrees Celsius, where the weight ratio of phase B to phase A is 1:5 to 5:1 to form a lyotropic lamellar liquid-crystalline mixed phase,
   c) diluting the mixed phase with an aqueous phase or polyol phase at a temperature of the aqueous phase or polyol phase below the melting or softening point of the active ingredient carrier by stirring without high-pressure homogenization to produce a desired end concentration of the dispersion, the dispersion containing lipid-based nanoparticles stabilized by an emulsifier monolayer or one or more membrane layers, the fragrances and/or aromas being included in the nanoparticles and/or in the emulsifier monolayer or the membrane layers and the dispersion being free of fragrance and/or aroma droplets.

2. The method according to claim 1, wherein the aqueous phase or the polyol phase A in step b) comprises an emulsifier.

3. The method according to claim 1, wherein the aqueous phase or the polyol phase A in step c) comprises an emulsifier.

4. The method according to claim 1, wherein the aqueous phase or the polyol phase A in step b) and in step c) comprises an emulsifier.

5. The method according to claim 1, wherein in step b) mixing is performed with a peripheral speed of a stirrer in the range of 1 m/s to 20 m/s.

6. The method according to claim 1, wherein in step c) stirring is performed with a peripheral speed by a stirrer in the range of 1 m/s to 20 m/s.

7. A composition for the targeted release of fragrances and/or aromas, prepared by the method of claim 1 in the form of a cosmetic, pharmaceutical, food or detergent composition.

8. The composition according to claim 7, wherein the fragrance and/or aroma is deposited at an interface of the lyotropic lamellar liquid crystalline phase with the highest absorbancy.

\* \* \* \* \*